United States Patent [19]

Cerri et al.

[11] Patent Number: 5,800,682
[45] Date of Patent: Sep. 1, 1998

[54] PROCESS FOR THE PRODUCTION OF DIFLUOROMETHANE

[75] Inventors: Gustavo Cerri, Boonton, N.J.; Kin Ching Kong, Woodside, N.Y.

[73] Assignee: AlliedSignal Inc., Morristown, N.J.

[21] Appl. No.: 731,038

[22] Filed: Oct. 8, 1996

[51] Int. Cl.⁶ .................... B01D 3/00; C07C 17/383
[52] U.S. Cl. .................. 203/99; 203/DIG. 19; 423/488; 570/178
[58] Field of Search .............. 203/99, 67, DIG. 19, 203/1, 39; 570/178, 177; 423/483, 488

[56] References Cited

U.S. PATENT DOCUMENTS

| | | | |
|---|---|---|---|
| 5,129,997 | 7/1992 | Schöttle et al. | 203/99 |
| 5,211,817 | 5/1993 | Adams et al. | 203/82 |
| 5,470,442 | 11/1995 | Mahler et al. | 203/66 |
| 5,495,057 | 2/1996 | Nam et al. | 570/167 |
| 5,523,015 | 6/1996 | Tsuda et al. | 203/50 |

FOREIGN PATENT DOCUMENTS

| | | |
|---|---|---|
| WO 94/21579 | 9/1994 | WIPO. |
| WO 94/21580 | 9/1994 | WIPO. |

*Primary Examiner*—Virginia Manoharan
*Attorney, Agent, or Firm*—Colleen D. Szuch; Jay P. Friedenson

[57] ABSTRACT

A liquid and vapor phase processes for the production of difluoromethane in which the risk of exposure to, and equipment fouling from, chlorofluoromethane is reduced. This reduction is accomplished from removing a sidestream containing monochloromonofluoromethane from a fluorination process distillation column.

10 Claims, No Drawings

PROCESS FOR THE PRODUCTION OF DIFLUOROMETHANE

FIELD OF THE INVENTION

The invention relates to liquid and vapor phase processes for the production of difluoromethane, HFC-32. In particular, the invention provides a process for producing HFC-32 in which the risk of personnel exposure to, and equipment fouling from, chlorofluoromethane, HCFC-31, is reduced.

BACKGROUND OF THE INVENTION

It is well known that HFC-32 may be used as a replacement for environmentally disadvantageous chlorofluorocarbon refrigerants. A number of methods for the liquid and vapor phase production of HFC-32 are also known. In some of the known methods, dichloromethane ("HCC-30") is fluorinated using hydrogen fluoride.

In the typical vapor or liquid phase process for production of HFC-32 by fluorinating HCC-30, a hydrogen fluoride feed is vaporized and superheated. The HCC-30 may also be vaporized. The feeds are then reacted in the presence of a fluorination catalyst to form a HFC-32 product stream in one or more isothermal or adiabatic reactors. The product stream produced contains the reaction products which include HFC-32, HCFC-31, and hydrogen chloride, unreacted feed stock such as hydrogen fluoride and HCC-30, and byproducts. Typically, the product stream is fed into a distillation column for separation.

The liquid flowing down the column, or bottoms stream, is a mixture of unreacted hydrogen fluoride, HCC-30, and the intermediate HCFC-31, which mixture may be recycled to the reactor after recovery. In this case, the top, or overhead, column stream comprises HFC-32, hydrogen chloride, hydrogen fluoride, and reaction byproducts. Alternatively, the HCFC-31 may be removed along with HFC-32, hydrogen chloride, and a part of the unreacted starting materials in the overhead of a first distillation column which is then fed into another column for further separation.

The HCFC-31 in the product stream is problematic because, in addition to being a potent mutagen, HCFC-31 can contribute to process equipment fouling. Methods to reduce the effects and/or production of HCFC-31 have been proposed. For example, WO 94/21579 discloses a process for producing HFC-32 in which a high hydrogen fluoride to HCFC-31 ratio is maintained in the separation step. The disclosed purpose for maintaining this ratio is to reduce the potential for HCFC-31 exposure and to eliminate the cost of facilities to prevent and detect leaks.

WO 94/21580 discloses a HFC-32 production process in which the use of a catalyst of zinc or a compound of zinc metal and a metal oxide, fluoride, or oxyfluoride is used. The use of these catalysts is disclosed as being directed to increasing HFC-32 yield, thereby decreasing HCFC-31 production.

However, none of the known HFC-32 production methods using HCC-30 as a starting material addresses the fact that even small amounts of HCFC-31 in the reactor product stream that is fed into the distillation column can build up to a great extent within the column. This build up occurs because HCFC-31 boils at a temperature between the boiling point of HFC-32 and that of the HCC-30 and hydrogen fluoride. The result of the build up is that the HCFC-31 concentration inside a major portion of the column can be much greater than the concentration in the product stream being fed into the column. Additionally, when the HCFC-31 is recycled back to the reactor, the HCFC-31 may be exposed to the heating surface of heat exchangers in the column reboiler and used to vaporize the reactor feed materials, which exposure may foul the heat exchangers. Therefore, a need exists for a HFC-32 production process that reduces the risk of exposure to HCFC-31 and reduces equipment fouling.

DESCRIPTION OF THE INVENTION AND PREFERRED EMBODIMENTS

The present invention provides a liquid or vapor phase process for producing HFC-32 in which HCFC-31 build up in process equipment is reduced. The process of the invention comprises withdrawing at an effective rate a sidestream comprising HCFC-31 from a distillation column into which a HFC-32 product stream comprising HFC-32, HCC-30, hydrogen fluoride and an amount of HCFC-31 is being fed. It has been discovered that when HCFC-31 is removed in this manner, the problem of HCFC-31 build up and potential exposure is diminished. Additionally, the method keeps the HCFC-31 out of the column reboiler where it can increase equipment fouling on its exposure to the hot heating surface.

By effective rate is meant a rate that is effective to remove an amount, on a weight basis, equal to or greater than, preferably greater than, more preferably 25 percent greater than, the amount of HCFC-31 in the product stream being fed into the column. For example, if the product stream contains 1 weight percent of HCFC-31 and is being fed into the column at 100 pounds per hour, the sidestream is withdrawn equal to or greater than about 1 pound per hour.

The HFC-32 product stream used in the process of this invention may be generated by any liquid or vapor phase fluorination reaction in which HCC-30 and hydrogen fluoride are reacted, which fluorination typically occurs in the presence of a fluorination catalyst. In addition to HFC-32, the product stream contains reaction products and intermediates which are HFC-32, hydrogen chloride, and HCFC-31, unreacted feed stock such as hydrogen fluoride and HCC-30, and reaction byproducts. One ordinarily skilled in the art will recognize that the amount of HCFC-31 in the product stream will depend on a number of factors including reaction conditions and the catalyst used. Typically, the product stream is fed into a distillation column that separates the desired HFC-32 along with hydrogen chloride from the hydrogen fluoride, HCFC-31, and HCC-30. Optionally, the hydrogen chloride may be removed in a separate distillation prior to feeding of the product stream into the column.

It as been discovered that, by withdrawing a sidestream containing HCFC-31 from an intermediate point in the column, the build up of HCFC-31 inside of the column is reduced and little or no HCFC-31 goes to the column reboiler. In one embodiment, the sidestream is a liquid sidestream that is a portion of the liquid refluxing down the column, which liquid includes HCFC-31, HCC-30, and hydrogen fluoride. In an alternative and preferred embodiment, the sidestream withdrawn from the column is a vapor sidestream that is a portion of the vapor moving up the column, which vapor contains HFC-32, HCFC-31, hydrogen fluoride, hydrogen chloride, and possibly HCC-30. More preferably, when the sidestream withdrawn is a portion of the vapor moving up the column, hydrogen chloride is removed from the product stream prior to feeding the product stream into the column. In any embodiment, the portion of either the liquid or vapor removed as a sidestream is such that an effective amount of HCFC-31 is removed from the column.

Removal of the HCFC-31 is achieved by withdrawing a sidestream from a location intermediate the column bottom and top. By column top and bottom is meant the physical top and bottom of the column. In cases in which the column has no physical top and bottom, such as a round distillation "column", top and bottom are meant to refer to the points of which the vapor and liquid, respectively, come off.

Preferably, the sidestream is taken from the point at which the highest concentration of HCFC-31 is present. This point will be intermediate between the feed point for the HFC-32 product stream and the top of the column when the column is being operated so that all of the HFC-32 is being separated with the top stream. If the column is being operated so that a portion of the HFC-32 is being separated with the bottoms stream, the highest concentration point for HCFC-31 will be between the feed point and the column bottom.

Any convenient method for withdrawing the side-stream from the column may be used to practice the process of the invention. For example, a vapor sidestream may be removed by installing a nozzle at the appropriate location on the column. As an example for a liquid sidestream, commercially available collection plates may be used to accumulate and withdraw the liquid through a nozzle on the column's side.

The HFC-32 product stream fed into the column may be the result of either a liquid or vapor phase process for producing HFC-32 in which HCC-30 is the starting material. In the vapor phase fluorination, fresh hydrogen fluoride and HCC-30 are fed into the reactor along with a recycle stream of unreacted hydrogen fluoride and HCC-30 as well as HCFC-31. One ordinarily skilled in the art can readily determine the amount of feed stock to be used. The reaction conditions also are well known to those ordinarily skilled in the art, the conditions generally being temperatures from about 170° to about 400° C. with pressures from about 0 atmospheres to over about 20 atmospheres. Residence time of the reactants in the reactor are from about 1 to about 100 seconds. Suitable vapor phase fluorination catalysts include, without limitation chromium, copper, aluminum, cobalt, magnesium, manganese, zinc, nickel and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$ and $NiCl_2/AlF_3$.

For liquid phase reactions, fresh hydrogen fluoride and HCC-30 are fed into the reactor along with a recycle stream of unreacted starting materials and HCFC-31. Feed stock amounts and reaction conditions for the liquid phase reaction are also well known to those ordinarily skilled in the art. Generally, temperatures of from about 70° to about 120° C. are used at about atmospheric to about 20 atmospheres of pressure. A catalyst stripper with a condenser may be used above the reactor to reflux catalyst along with a portion of the reactants back into the reactor. The product stream fed into the column may be the distillate from the stripper. Suitable fluorination catalysts include, without limitation, antimony, titanium, tin, niobium, and tantalum halides.

The process of the invention will be clarified further by a consideration of the following examples that are purely exemplary.

EXAMPLES

For the following examples, vapor-liquid equilibrium ("VLE") data were determined from the laboratory analysis of the vapor and liquid composition of a product stream at different temperatures and pressures. The data were then fitted using the Universal Quasi-Chemical Functional Group Activity Coefficient ("UNIFAC") as the model to represent the VLE data for the mixture. The UNIFAC model was then used in computer simulations to demonstrate the reduction of HCFC-31 that can be achieved in a distillation column by withdrawing a sidestream containing HCFC-31.

Example 1

A product stream from the production of HFC-32 flowing from the reactor at a rate of 100 lb/hr and containing approximately 2.5% weight percent HCFC-31 is fed into a distillation column with 40 ideal separation stages. The amount of HCFC-31 fed into the column is 2.5 lb/hr. The column is operated to separate HCl and HFC-32 in the column top and HF, HCC-30, and HCFC-31 in the bottom. Table 1 shows the calculated HCFC-31 build-up within the distillation apparatus.

TABLE 1

| Column Stages | Wt % HCFC-31 in Vapor | Wt % HCFC-31 in Liquid |
|---|---|---|
| 1–2 | <0.5 | <2.5 |
| 3 | 1.0 | 6.4 |
| 4–7 | 6–80 | 27–93 |
| 8–20 | 86–89 | 90–96 |
| 21–23 | 76–84 | 52–82 |
| 24–38 | 80–83 | 46–52 |
| 39–40 | 55–74 | 15–33 |
| Liquid to Reboiler | Not Applicable | 15 |
| Reboiler | 23 | 4 |

As can be seen from Table 1, the HCFC-31 concentration is above the product stream concentration by weight over 90% of the column stages.

Example 2

The product stream of Example 1 is used. A liquid sidestream is taken at a rate of approximately 3 lb/hr from an intermediate stage located above the column feed to withdraw a portion of the liquid refluxing down the column. Table 2 shows the concentration of HCFC-31 in the distillation apparatus.

TABLE 2

| Column Stages | Wt % HCFC-31 in Vapor | Wt % HCFC-31 in Liquid |
|---|---|---|
| 1–2 | <0.5 | <2.5 |
| 3 | 1.0 | 6.3 |
| 4–8 | 6–77 | 28–87 |
| 9–13 | 81–83 | 28–90 |
| 14–16 | 16–74 | 3–55 |
| 17–22 | <0.3 | <0.5 |
| 23–40 | <0.2 | <0.03 |
| Liquid to Reboiler | Not Applicable | Nil |
| Reboiler | Nil | Nil |

As shown in Example 2, the concentration of HCFC-31 is above the product stream concentration in only about 35% of the column stages and substantially no HCFC-31 is found in the reboiler.

Example 3

The product stream of Example 1 is used. A vapor sidestream is taken at a rate of approximately 3 lb/hr from an intermediate stage located above the column feed to withdraw a portion of the vapor moving up the column. Table 3 shows the concentration of HCFC-31 in the distillation apparatus.

TABLE 3

| Column Stages | Wt % HCFC-31 in Vapor | Wt % HCFC-31 in Liquid |
| --- | --- | --- |
| 1-2 | 0.5 | 2.5 |
| 3 | 1.0 | 6.4 |
| 4-8 | 6-77 | 27-87 |
| 9-12 | 81-83 | 83-89 |
| 13-16 | 6-77 | 1-67 |
| 16-31 | <2 | <0.2 |
| 32-40 | <0.1 | <0.1 |
| Liquid to Reboiler | Not Applicable | Nil |
| Reboiler | Nil | Nil |

As shown on table 3, the HCFC-31 concentration is above the product stream concentration in only about 35% of the column stages and substantially no HCFC-31 is found in the reboiler.

What is claimed is:

1. A process for reducing monochloromonofluoromethane in a product stream comprising difluoromethane, dichloromethane, hydrogen fluoride and monochloromonofluoromethane comprising feeding said product stream to a distillation column, withdrawing from the distillation column a top product comprising difluoromethane, a bottom product comprising dichloromethane and hydrogen fluoride, and a sidestream comprising monochloromonofluoromethane, wherein the sidestream is withdrawn at a rate such that an amount greater than or equal to the amount of monochloromonofluoromethane in the product stream is being removed from the distillation column.

2. The process of claim 1 wherein the sidestream is withdrawn at a rate such that an amount greater than the amount of monochloromonofluoromethane in the product stream is being removed from the distillation column.

3. The process of claim 2 wherein the sidestream is withdrawn at a rate such that an amount of at least 25 percent greater than the amount of monochloromonofluoromethane in the product stream is being removed from the distillation column.

4. A process for reducing monochloromonofluoromethane in a product stream comprising difluoromethane, dichloromethane, hydrogen fluoride and monochloromonofluoromethane comprising feeding said product stream to a distillation column, withdrawing from the distillation column a top product comprising difluoromethane, a bottom product comprising dichloromethane and hydrogen fluoride, and a liquid sidestream comprising monochloromonofluoromethane wherein the sidestream is withdrawn at a rate such that an amount greater than or equal to the amount of monochloromonofluoromethane in the product stream is being removed from the distillation column.

5. The process of claim 4 wherein the rate at which the sidestream is withdrawn is such that an amount of at least about 25 percent greater than the amount of monochloromonofluoromethane in the product stream is being removed from the column.

6. A process for reducing monochloromonofluoromethane in a product stream comprising difluoromethane, dichloromethane, hydrogen fluoride and monochloromonofluoromethane comprising feeding said product stream to a distillation column, withdrawing from the distillation column a top product comprising difluoromethane, a bottom product comprising dichloromethane and hydrogen fluoride, and a vapor sidestream comprising monochloromonofluoromethane wherein the sidestream is withdrawn at a rate such that an amount greater than or equal to the amount of monochloromonofluoromethane in the product stream is being removed from the distillation column.

7. The process of claim 6 wherein the rate at which the sidestream is withdrawn is such that an amount of at least about 25 percent greater than the amount of monochloromonofluoromethane in the product stream is being removed from the column.

8. The process of claim 6, wherein the product stream further comprises hydrogen chloride.

9. The process of claim 8 further comprising removing hydrogen chloride from the product stream prior to feeding the product stream into the distillation column.

10. The process of claim 9 wherein the sidestream is withdrawn at a rate such that an amount of at least about 25 percent greater than the amount of monochloromonofluoromethane in the product stream is being removed from the distillation column.

\* \* \* \* \*